United States Patent [19]

Ljungdahl et al.

[11] 4,292,406

[45] Sep. 29, 1981

[54] ANAEROBIC THERMOPHILIC CULTURE SYSTEM

[75] Inventors: Lars G. Ljungdahl, Athens, Ga.; Jürgen K. W. Wiegel, Göttingen, Fed. Rep. of Germany

[73] Assignee: The United States of America as represented by the United States Department of Energy, Washington, D.C.

[21] Appl. No.: 74,286

[22] Filed: Sep. 11, 1979

[51] Int. Cl.³ .............................................. C12P 39/00
[52] U.S. Cl. ...................................... 435/42; 435/162; 435/163; 435/165; 435/254; 435/801; 435/842
[58] Field of Search ............... 435/161, 162, 163, 165, 435/801, 842, 172, 42

[56] References Cited

U.S. PATENT DOCUMENTS 4,094,742  6/1978  Bellamy ................................ 435/42

OTHER PUBLICATIONS

Smith et al. "Bergys Manual of Determinative Bacteriology", Williams & Wilkins Co. Publishers, (1974), pp. 551 and 572.
McBee, "The Characteristics of *Clostridium thermocellum*" J. of Bacteriology, vol. 67 (1954) pp. 505–506.

*Primary Examiner*—R. B. Penland
*Attorney, Agent, or Firm*—Allen F. Westerdahl; Raphael V. Lupo; James E. Denny

[57] ABSTRACT

A mixed culture system of the newly discovered microorganism *Thermoanaerobacter ethanolicus* ATCC31550 and the microorganism *Clostridium thermocellum* ATCC31549 is described. In a mixed nutrient culture medium that contains cellulose, these microorganisms have been coupled and cultivated to efficiently ferment cellulose to produce recoverable quantities of ethanol under anaerobic, thermophilic conditions.

6 Claims, No Drawings

ANAEROBIC THERMOPHILIC CULTURE SYSTEM

The invention is the result of a contract with the U.S. Department of Energy.

BACKGROUND OF THE INVENTION

This invention relates to a mixed culture system of anaerobic thermophilic microorganisms and more particularly, to a mixed culture of the newly discovered thermophilic glycolytic anaerobe *Thermoanaerobacter ethanolicus* and *Clostridium thermocellum*. Further, the invention relates the novel process for producing ethanol from cellulose by fermentation in a nutrient medium with a mixed culture prepared from biologically pure cultures of *Thermoanaerobacter ethanolicus* and *Clostridium thermocellum*. The invention is the result of a contract with the U.S. Department of Energy.

Relatively few anaerobic microorganisms have been isolated and characterized that grow on carbohydrates (are glycolytic) and yield ethanol under thermophilic and extreme thermophilic conditions. Representative examples of well-characterized glycolytic anaerobic bacteria that will grow in a nutrient culture in the thermophilic to extreme thermophilic ranges belong to the genus Clostridium and include: *C. thermoaceticum, C. tartarivorum, C. thermosaccharolyticum, C. thermocellum, C. thermocellulaseum,* and *C. thermohydrosulfuricum*. Strains of the latter organism have been isolated and characterized by J. Wiegel and L. G. Ljungdahl (See Abstract I 75 of the Abstract of the Annual Meeting of the American Society of Microbiology, Las Vegas, Nev., USA, 1978 and J. Bacteriology, September 1979 in press). A neotype strain of *C. thermohydrosulfuricum* E 100-69 was isolated from the liquors of an Austrian sugar beet factory by F. Hollaus and U. Sleytr (See Arch. Mikrobiol. 86: 129–146, 1972).

In addition to these well known species, two non spore-forming strains representing new species of a new genus have been isolated and characterized. The newly discovered thermophilic anaerobes were isolated in biologically pure cultures and designated as *Thermoanaerobacter ethanolicus*. A representative stain of this new microorganism in a biologically pure subculture, designated JW 200, has been deposited in the patent strain collection of the American Type Culture Collection, Rockville, Md., USA. ATCC 31550 is the accession number assigned by the American Type Culture Collection to this strain. In the isolation, purification and characterization of this newly discovered species, which is not a Clostridium, it has been found that the new species is an efficient producer of ethanol from various carbohydrates, in particular, the most common mono- and di-saccharides.

*Thermoanaerobacter ethanolicus* has been disclosed and claimed in a copending application Ser. No. 74,287 filed on the same date by the same inventors. As disclosed in that application, *T. ethanolicus* is cultured in aqueous nutrient medium under anaerobic, thermophilic conditions and is used in a novel process for producing ethanol which comprises subjecting carbohydrates, particularly the saccharides, to fermentation action of the newly isolated microorganism *T. ethanolicus* in a biologically pure culture to form ethanol and recovering said ethanol. While *T. ethanolicus* efficiently ferments a variety of sugars to yield ethanol, one of the characteristics of the anaerobe is that it does not ferment cellulose. It is known that the anaerobic microorganism *Clostridium thermocellum,* isolated in 1950, ferments cellulose to hydrogen, carbon dioxide, ethanol, formate, acetate, lactate and to a lesser degree, dicarboxylic acids at thermophilic temperatures. (See McBee, R. H. 1950. *The anaerobic thermophilic cellulolytic bacteria.* Bacteriol. Rev. 14:51-63). However, it has been found that in the clostridial cellulase system produced of this fermentation, some of the products formed by the action of cellulase, such as cellobiose, and glucose tend to inhibit the growth of *C. thermocellum* thereby repressing the cellulase enzyme system. Other sugars possibly present in a fermentation medium like lactose may also inhibit cellulase. While *C. thermocellum* will utilize these sugars, growth is slow and the yield of products, such as ethanol, is small. Thus, *C. thermocellum* in biologically pure form, while useful for the break down of the cellulose, will not efficiently ferment the sugar substrate produced and that, in fact, the fermentation is inhibited by the substrate accumulation. A newly isolated representative strain of *C. thermocellum* designated JW 20 has been deposited in the patent strain collection of the American Type Culture Collection, Rockville, Md., USA. ATCC 31549 is the accession number assigned to this strain of *C. thermocellum*.

These microorganisms are, of course, of use for the possible anaerobic fermentation of various carbohydrates, such as the saccharides, and in mixed cultures to efficiently break down cellulose for the production of ethanol and other products of fermentation under thermophilic conditions. Yeast (Saccharomyces species) fermentation of sugar, as is well known, ordinarily must be conducted at less than about 37° C. under semiaerobic conditions to yield ethanol. Further, the conditions must be carefully controlled to avoid contamination of harmful bacteria, fungi, and molds.

SUMMARY OF THE INVENTION

Accordingly, it is an object of the present invention to provide a novel mixed nutrient culture system of microorganisms that produce ethanol under anaerobic thermophilic conditions. It is also an object of the invention to provide a process for producing ethanol by coupling of biologically pure cultures of certain thermophilic anaerobes. It is also an object to couple biologically pure cultures of the newly discovered microorganism *T. ethanolicus* and the known microorganism *C. thermocellum* for the efficient fermentation of cellulose to produce ethanol therefrom.

In accordance with the present invention there is provided a mixed culture system of the newly discovered microorganism *T. ethanolicus* and the microorganism *C. thermocellum*. In a mixed nutrient culture medium that contains cellulose, these microorganisms have been coupled and cultivated to efficiently ferment said cellulose to produce recoverable quantities of ethanol. This novel fermentation is conducted under anaerobic, thermophilic conditions. Further the novel process of the present invention is a process for producing ethanol directly from cellulose which comprises subjecting said cellulose to the fermentation action of the newly isolated microorganism *T. ethanolicus* coupled with the microorgansm *C. thermocellum* in a mixed nutrient culture to form ethanol and recovering said ethanol. This process is conducted under anaerobic, thermophilic conditions.

For the purpose of this specification, the term "thermophilic" refers to a culture temperature between about 45° C. to 70° C.

While it is not intended that the process of the present invention be limited to any particular theory, it will be apparent from the following description and example, that the coupling of *T. ethanolicus* and *C. thermocellum* greatly enhances the cellulose breakdown, prevents inhibition of the fermentation as hereinabove described, and shifts the fermentation toward the production of ethanol.

DETAILED DESCRIPTION OF THE PREFERRED EMBODIMENT

As was described in the copending application Ser. No. 74,287 hereinabove cited the microorganism *T. ethanolicus* was discovered in and isolated from mud samples of hot springs in Yellowstone National Park, Wyo., U.S.A. One strain JW-201 was isolated from an acidic spring, the Dragon Mouth, with a pH of about 5.5 and the second strain JW 200 from a alkaline spring, White Creek, with a pH of about 8.8. The strains are very similar and were discovered in association with the anaerobic thermophilic Clostridia strains hereinabove mentioned.

Although the new microorganism strains share the ability to ferment certain carbohydrates at thermophilic temperatures with the Clostridia mentioned above, they do not form spores and are therefore excluded from the genus Clostridium. In view of the morphology and fermentation characteristic, these new strains are deemed a new genus and species designated *Thermoanaerobacter ethanolicus*, ATCC 31550 being representative of these strains.

Isolation of *T. ethanolicus* in biologically pure form was accomplished using the anaerobic technique according to Hungate, Bacteriol. Rev. 14: 1-49 as modified by Bryant and Robinson, J. Dairy Science 44; 1446-1456, which technique will be familiar to those skilled in the art. The medium used for isolation and enrichment cultures and to maintain the isolated strains has the following preferred compositions: $KH_2PO_4$, 1.5 g/l; $Na_2HPO_4 \cdot 12H_2O$, 4.2 g/l; $NH_4Cl$, 0.5 g/l; $MgCl_2$, 0.18 g/l; yeast extract (Difco), 2.0 g/l; glucose, 8.0 g/l; and Wolfe's mineral solution, 5 ml. The medium is prepared under anaerobic conditions and must be stored under an atmosphere of an inert gas, such as nitrogen or argon. The pH of the medium is in the range of about 6.8 to 7.8, preferably 7.3, and is adjusted as required with a sterile, anaerobic NaOH or HCl solution. Stock cultures are maintained on the same medium solidified with 2% agar and stored at 4° C. Liquid medium cultures can be stored at $-18°$ C. after the addition of an equal volume of glycerol.

Although in the exemplary nutrient medium, glucose is the preferred carbohydrate substrate, other monosaccharides, such as, xylose, ribose, mannose, fructose and galactose, and disaccharides, such as sucrose, lactose, maltose, and cellobiose can be used. Growth also occurs on pyruvate, pectin, and starch. It should be noted that *T. ethanolicus* requires yeast extract for growth. Without yeast extract, no growth was obtained in subsequent subcultures. Although growth is much less than in the presence of glucose, yeast extract concentrations above 0.5% can serve as the only carbon, nitrogen and energy source. However, as will be shown in the Example, pure cultures of *T. ethanolicus* do not ferment cellulose.

Biologically pure cultures of *Thermoanaerobacter ethanolicus* ATCC 31550 (JW 200) for use in the present invention can be conveniently prepared using the same nutrient medium as used for isolation under anaerobic conditions at temperatures between about 36° C. and 78° C. with the optimum temperature for growth being about 68° C. Doubling time at 68° C. is about 90 minutes. Such growth is not pH dependent in that growth occurs in the very wide pH range of from 4.5 to 9.8. For optimum growth, the pH of the medium should be between about 5.7 and 8.6, with the preferred pH being about 7.3.

*Clostridium thermocellum* has been isolated, cultivated and characterized by a number of investigators. In addition to the McBee, reference above noted, reference is made to the following:

Alexander, J. L. 1969. Purification and specificity of cellobiose phosphorylase from *Clostridium thermocellum*. J. Biol. Chem. 243:2899-2904.

Patni, N. J. and J. L. Alexander. 1971a. Utilization of glucose by *Clostridium thermocellum;* Presence of glucokinase and other glycolytic enzymes in cell extracts. J. Bacteriol. 105:220-225.

Patni, N. J. and J. K. Alexander. 1971b. Catabolism of fructose and mannitol in *Clostridium thermocellum*. Presence of phosphoenolpyruvate: fructose phosphotransferase, fructose 1-phosphate kinase, phosphoenolpyruvate; mannitol phosphotransferase and mannitol 1-phosphate dehydrogenase in cell extracts. J. Bacteriol. 105:226-231.

Lee, B. H. and T. H. Blackburn. 1975. Cellulose production by a thermophilic Clostridium species. Appl. Microbiol. 30:346-353.

Ng, T. K., P. J. Weimer and J. G. Zeikus. 1977. Cellulolytic and physiological properties of *Clostridium thermocellum*. Arch. Microbiol. 114:1-7.

A strain of *C. thermocellum* ATCC 31549 (JW 20) has been isolated by us from a cotton bale from Louisiana, U.S.A. As with *T. ethanolicus*, this strain of *C. thermocellum* was isolated in biologically pure form using the Hungate technique as modified by Bryant and Robinson. The nutrient medium hereinabove described that was used for *T. ethanolicus*, was used for isolation and enrichment of *C. thermocellum*, except that cellulose in the form of paper derived from wood pulp, (10.8 g/l) was used instead of glucose for the substrate and the amount of yeast extract was increased to 5.0 g/l. The medium is prepared under anaerobic conditions and must be stored under an atmosphere of an inert gas, such as nitrogen or argon. The pH of the medium is in the range of about 6.8 to 7.8, preferably 7.3.

Cellulose, the naturally occurring polymer of glucose, is available from a variety of sources, both in an untreated, impure, natural state, such as in the form of plant tissue, and in a hydrolyzed or treated form, such as paper prepared from wood pulp. Those skilled in the art will recognize that treatment of natural, impure cellulose is desirable for more efficient fermentation of the cellulose material. For a description of the various types of cellulose and preferred methods of preparation for fermentation see U.S. Pat. No. 4,094,742. For the purposes of this specification, cellulose that has been treated physically and chemically to break down the existing lignin protective covering and expose the cellulose component is the preferred form of cellulose material for efficient fermentation. Previously treated waste cellulose material, such as paper, is particularly preferred for fermentation. Although treated cellulose sources are preferred for fermentation, it is not intended that the present invention be limited to those sources because the mixed culture provides a means for the biological breakdown of cellulose material from a variety of sources. As shown in Example 2 and Table III, below, the present mixed culture will ferment diverse cellulose substrates to produce ethanol.

C. thermocellum can be conveniently grown in the same substrate medium as used for isolation under anaerobic conditions at temperatures between 45° C. and 65° C. with the optimum temperature for growth being about 60° C.

The same cellulose containing medium that is used for the isolation and cultivation of C. thermocellum is used for the coupled fermentation of cellulose using T. ethanolicus and C. thermocellum under anaerobic thermophilic conditions. As will be shown in the following Example I, such direct fermentation of cellulose (paper) will provide a significant yield of ethanol. As high as 1.46 mole of ethanol is produced per glucose unit of cellulose at a temperature of 60° C. and at a pH of 7.5 under anaerobic conditions. Ethanol product from this fermentation can be recovered by conventional distillation techniques.

The following specific examples will serve to further illustrate the present invention in its preferred embodiment.

EXAMPLE I

Cellulose Fermentation

Cellulose fermentations were conducted using T. ethanolicus (ATCC 31550) and C. thermocellum (ATCC 31549) in pure cultures and in mixed cultures. All fermentations were conducted under an argon atmosphere at 60° C. for 168 hours. Incubations were conducted in 50 ml of the medium hereinabove described with 540 mg of cellulose (in the form of paper derived from wood pulp instead of glucose) and with 0.5% yeast extract. Initial pH 7.5. The results of these fermentations are shown in the following Table.

TABLE I

| | | C. ther-mocellum | T. etha-nolicus | C. thermocellum + T. ethanolicus | |
|---|---|---|---|---|---|
| | | | | A | B |
| Cellulose fermented | mg | 351 | 4 | 500 | 372 |
| | mM | 2.13 | 0.024 | 3.05 | 2.27 |
| Ethanol produced | mM | 1.79 | 0.05 | 4.45 | 2.33 |
| Ethanol (mol) glucose residue of cellulose | | 0.84 | — | 1.46 | 1.05 |

In Experiment A, the pH was controlled during fermentation and maintained at 7.5, whereas in Experiment B, the pH was allowed to decrease due to formation of acids.

This example shows that coupling C. thermocellum with T. ethanolicus greatly enhances the rate of cellulose breakdown and that the coupling shifts the fermentation toward a significantly greater production of ethanol. The example also indicates that better results are obtained when the pH is controlled throughout the fermentation.

EXAMPLE 2

Fermentation Using Diverse Cellulose Substrates

Diverse sources of cellulose, some treated and some untreated, were fermented with mixed cultures of C. thermocellum, ATCC 31549, and T. ethanolicus, ATCC 31550. The fermentations were for the times indicated in 10 ml cultures containing 100 mg of the cellulose sample at 60° C., pH 6.8 and under a nitrogen atmosphere. The results are shown in the following Table II.

TABLE II

| Substrate | Fermentation Time Days | Ethanol Yield mg |
|---|---|---|
| Filter paper, Whatman #1 | 7 | 31.8 |
| Wood chips, steam exploded | 7 | 19.4 |
| Hardwood, acid hydrolyzed | 7 | 25.4 |
| Palm tree, core | 7 | 25.4 |
| Bermuda grass, coast-cross | 21 | 15.2 |
| Wheat straw | 21 | 16.1 |
| Corn stover | 21 | 8.3 |

What is claimed is:

1. The mixed culture system comprising a biologically pure strain of the microorganism Thermoanaerobacter ethanolicus, having the identifying characteristics of ATCC 31550 and a biologically pure strain of the microorganism Clostridium thermocellum, having the identifying characteristics of ATCC 31549, said culture system having the ability to produce ethanol in recoverable quantities upon fermentation in an aqueous nutrient culture containing cellulose material.

2. A mixed anaerobic, thermophilic culture system of the microorganisms Thermoanaerobacter ethanolicus and Clostridium thermocellum each of said microorganisms isolated in biologically pure culture, having the identifying characteristics of ATCC 31550 and 31549, respectively, and having the ability, when combined in a mixed culture system, to yield ethanol as a major product constituent upon fermentation in an aqueous nutrient medium containing cellulose material.

3. A process which comprises cultivating Thermoanaerobacter ethanolicus and Clostridium thermocellum having the identifying characteristics of ATCC 31550 and 31549, respectively, in a mixed nutrient culture medium containing cellulose material under anaerobic, thermophilic conditions until a recoverable quantity of ethanol is produced.

4. The process for producing ethanol from cellulose material which comprises subjecting said cellulose material to the fermentation action of anaerobic microorganisms Thermoanaerobacter ethanolicus and Clostridium thermocellum having the identifying characteristics of ATCC 31550 and 31549, respectively, in a mixed nutrient culture to form ethanol and recovering said ethanol.

5. The process of claim 4 wherein said process in conducted under thermophilic conditions.

6. A process of claim 4, wherein said process is conducted at a pH range of between 6.8 and 7.8 and at a temperature of between about 45° C. and 70° C.

* * * * *